(12) United States Patent
Cary

(10) Patent No.: US 8,864,742 B2
(45) Date of Patent: Oct. 21, 2014

(54) CATHETER LOCKING COMPOSITION

(75) Inventor: Douglas D. Cary, Great Falls, VA (US)

(73) Assignee: Cary Pharmaceuticals Inc., Great Falls, VA (US)

(*) Notice: Subject to any disclaimer, the term of this patent is extended or adjusted under 35 U.S.C. 154(b) by 109 days.

(21) Appl. No.: 13/126,068

(22) PCT Filed: Nov. 12, 2009

(86) PCT No.: PCT/US2009/064174
§ 371 (c)(1),
(2), (4) Date: Apr. 26, 2011

(87) PCT Pub. No.: WO2010/056836
PCT Pub. Date: May 20, 2010

(65) Prior Publication Data
US 2011/0208159 A1 Aug. 25, 2011

Related U.S. Application Data

(60) Provisional application No. 61/113,816, filed on Nov. 12, 2008.

(51) Int. Cl.
*A61M 31/00* (2006.01)
*A61K 31/19* (2006.01)
*A61L 29/16* (2006.01)
*A61L 33/00* (2006.01)
*A61L 29/14* (2006.01)
*A61M 25/00* (2006.01)

(52) U.S. Cl.
CPC ............ *A61L 29/14* (2013.01); *A61L 2300/42* (2013.01); *A61L 29/16* (2013.01); *A61L 33/0011* (2013.01); *A61M 2025/0019* (2013.01); *A61L 2300/21* (2013.01)
USPC .......................................... 604/508; 514/574

(58) Field of Classification Search
None
See application file for complete search history.

(56) References Cited

U.S. PATENT DOCUMENTS

| 4,929,242 A | 5/1990 | Desecki et al. |
| 6,685,694 B2 | 2/2004 | Finch et al. |
| 6,958,049 B1 * | 10/2005 | Ash .............................. 604/28 |
| 2005/0215978 A1 | 9/2005 | Ash |

FOREIGN PATENT DOCUMENTS

EP 1688154 8/2006

OTHER PUBLICATIONS

L.W. Young, International Search Report in PCT/US09/64174 mailed Jan. 12, 2010, 2 pages, USPTO.
L.W. Young, Written Opinion in PCT/US09/64174 mailed Jan. 12, 2010, 4 pages, USPTO.
Extended European Search Report in European Application No. 09826732.1 (Dec. 5, 2013).

* cited by examiner

*Primary Examiner* — Abigail Fisher
*Assistant Examiner* — Daniel L Branson
(74) *Attorney, Agent, or Firm* — Florek & Endres PLLC

(57) ABSTRACT

The present invention relates to locking compositions, kits containing the locking compositions and methods for maintaining the patency of vascular access devices or intravascular delivery devices employing the locking compositions. The locking compositions contain water, an anticoagulant and a viscosity agent and are free of heparin and alcohol.

12 Claims, No Drawings

CATHETER LOCKING COMPOSITION

CROSS-REFERENCE TO RELATED APPLICATION

This application is a U.S. National Stage filing under 35 U.S.C. 371 of International Application No. PCT/US2009/064174, filed Nov. 12, 2009, which claims the benefit of provisional application Ser. No. 61/113,816, filed on Nov. 12, 2008.

BACKGROUND OF THE INVENTION

1. Field of the Invention

The present invention relates to locking compositions, kits containing the locking compositions and methods for maintaining the patency of a vascular access device or intravascular delivery device that employs the locking compositions. The locking composition in accordance with the present invention comprises a carrier such as water, an anticoagulant and a viscosity agent. The locking compositions useful in the present invention are free of heparin. The compositions useful in the present invention may also be hypertonic and exhibit a density and viscosity greater than the blood of the subject with the vascular access device or intravascular delivery device.

2. Description of the Related Art

Indwelling vascular catheters represent an important and common procedure performed in daily medical practice. Intravascular catheters are routinely flushed with an anticoagulant solution to prevent clotted blood from clogging the catheter lumen. In cases where catheters are left in place for long term use, flushing constitutes an important, but labor intensive, aspect of catheter care. In current medical practice, a solution of heparin in saline (e.g., sodium chloride in solution) is commonly used for this purpose, although saline alone is also used.

Although effective in preventing clotting within catheters, a significant disadvantage of such saline or heparin solutions is that they must be administered frequently, e.g., the catheter must be flushed every 4-8 hours to prevent blockage. This frequency of administration represents a considerable labor effort for healthcare providers. Furthermore, because heparin is extracted from animal tissues, it poses a potential risk of zoonotic disease transmission, as well as other quality and performance problems.

It is estimated that more than 250 million peripheral and central catheters are used each year in clinical medicine. Considering a conservative treatment regiment, a cumulative total of 900 million saline heparin flushes are administered each year. Peripheral and central indwelling catheters are used to provide an access site to the patient (subject) to administer intermittent medications, I.V. fluids or to draw blood samples. In order to maintain patency (free of blood clots) of the catheter tip a solution of heparin (10 to 100 IU)/saline or saline alone are used to fill the catheter when it is not being used. However, as many as 15% of all intermittent sites established continue to be lost due to coagulation buildup and eventual lumen blockage. An example catheter lock solution for solving these problems includes a combination of ingredients that will provide improved protection of the catheter to clot formation while being cost effective.

U.S. Pat. No. 4,929,242 describes a method and solution for maintaining the patency of a catheter during intermittent drug therapy administration. The disclosed solution consists of a carrier such as water and a density/osmolality adjusting material such as glycerol, dextrose and/or sodium chloride. The disclosed solution is adjusted to have a density and osmolality similar to whole blood.

U.S. Pat. No. 6,685,694 discloses methods and kits for locking and/or disinfecting subcutaneously and transcutaneously implanted catheters. The disclosed methods and kits require the addition of a lower alcohol to the catheter lumen in an effort to prevent fouling and plugging of the lumen.

Although the methods and compositions described in U.S. Pat. Nos. 4,929,242 and 6,685,694 are reported to improve fouling and plugging of catheter lumens, there is still a need for improvement. Accordingly, a continuing and unmet need exists for new and improved locking compositions for vascular access devices or intravascular delivery devices.

It is an object of the present invention to provide a composition for maintaining the patency of a vascular access device or intravascular delivery device that does not employ heparin.

It is a further object of the present invention to provide a composition for maintaining the patency of a vascular access device or intravascular delivery device that prevents fouling and/or plugging of the vascular access device or intravascular delivery device for more than 8 hours, preferably more than 12 hours and most preferably more than 16 hours.

It is another object of the present invention to provide a composition for maintaining the patency of a vascular access device or intravascular delivery device that exhibits a density greater than the density of whole blood and that is hypertonic.

It is also an objective of the present invention to provide a composition for maintaining the patency of a vascular access device or intravascular delivery device that exhibits antimicrobial properties.

It is also a further objective of the present invention to provide a composition for maintaining the patency of a vascular access device or intravascular delivery device that is stable upon storage for at least six months, preferably at least a year or longer, prior to use in a subject.

It is still an additional objective of the present invention to provide a composition for maintaining the patency of a vascular access device or intravascular delivery device that may be terminally sterilized after its preparation and prior to use in a subject.

SUMMARY OF THE INVENTION

The above objectives and others are obtained by the present invention which is a locking composition comprising a carrier, a viscosity increasing agent and an anticoagulant. The locking composition should be a hypertonic composition compared to a subject's blood plasma and should exhibit a density and viscosity greater than a subject's blood.

The locking composition should prevent fouling and plugging of a subject's vascular access device or intravascular delivery device for at least about eight (8) hours, preferably about 8 to about 24 hours, and provide long term storage prior to use, preferably at least six months to a year or longer.

In one embodiment of the present invention, the locking composition comprises a carrier, such as water, about 35% to about 70%, preferably about 40% to about 60% and most preferably about 45% to about 55%, of a viscosity-increasing agent and about 1% to about 10% of an anticoagulant, preferably about 2% to about 8% and most preferably about 3% to about 6%, wherein the anticoagulant is not heparin and the composition is free of alcohols.

The present invention also includes a method of using the locking composition to maintain the patency of a vascular access device or intravascular delivery device. The method comprises the steps of: inserting a vascular access device or intravascular delivery device such as an I.V. catheter, hemodialysis catheter, central venous catheter, cannulae, tube, injection ports, hollow needles, and the like into a subject, preferably a mammal such as a dog, cat, horse, pig or cow and most preferably a human; and inserting the locking composition of the present invention into the lumen of the vascular access device or intravascular delivery device. The locking composition can be inserted into the lumen of the vascular access device or intravascular delivery device by a syringe, preferably a prefilled syringe that is packaged with the vascular access device or intravascular delivery device.

In one embodiment of the present invention, the prefilled syringe also contains an appropriate amount, i.e., a predetermined and premeasured amount of the locking composition. For example, if the lumen of a catheter has a volume of 5 ml, the prefilled syringe accompanying the catheter will contain 5 ml of the locking composition. Alternatively, the locking composition may be provided in a standard glass or plastic container such as a bottle, vial or bag. The container may contain single or multiple doses of the locking composition. Appropriately measured amounts of the composition may be removed from the container and inserted into the lumen of the catheter.

Another embodiment of the present invention is a kit comprising a container comprising the locking composition for maintaining the patency of a vascular access device or intravascular delivery device and an instruction set describing the use of the locking composition. The container may comprise about 1 ml to about 500 ml of the locking composition or other appropriate amount of the locking composition such as 10, 20, 25, 50 or 100 ml. The kit may further comprise a vascular access device or intravascular delivery device such as a catheter and a syringe for filling the vascular access device or intravascular delivery device with the locking composition once the vascular access device or intravascular delivery device has been inserted into a subject. In a further aspect of this embodiment, the container comprising the locking composition and the syringe may be the same component and contain a premeasured amount of the composition for filling the lumen of the vascular access device or intravascular delivery device once inserted into the subject. Once the contents of the container or syringe are emptied into the lumen of the vascular access device or intravascular delivery device, the container or syringe is discarded.

Another embodiment of the present invention is a novel blood-compatible, anticoagulant citrate-glycerol solution suitable for use in vascular access device or intravascular delivery device, and intravenous catheters in particular. As described herein, embodiments of the aspect of the invention are aqueous solutions comprising about 1% to about 10%, preferably about 2% to about 8% and most preferably about 3% to about 6%, of a citrate and about 35% to about 70%, preferably about 40% to about 60% and most preferably about 45% to about 55% of glycerol. These embodiments have been shown to exhibit good anticoagulant properties compared to solutions containing 100 IU/ml (HEP-LOCK™).

A further embodiment of the present invention described herein is a blood-compatible, anticoagulant composition consisting essentially of water, about 2% to about 6%, preferably about 3% to about 5% of a citrate and about 40% to about 60%, preferably about 45% to about 55%, glycerol. This embodiment is preferably free of heparin and alcoholic compounds, especially $C_1$ to $C_{12}$ alcohols. This embodiment may be prepared by dissolving the citrate in a mixture of water and glycerol. This embodiment may be sterilized after preparation, and is compatible with a subject's blood and prevents coagulation (clotting) of the blood or blood products for about 8-48 hours, preferably about 8-24 hours and most preferably at least about 8 hours.

A still further embodiment of the present invention includes a method for manufacturing the locking compositions comprising the steps of combining the viscosity increasing agent with an aqueous mixture of the citrate. The pH of the combination may be adjusted by the addition of pharmaceutically acceptable acids or bases until a range of about 5.8 to about 6.8, preferably about 6.0 to about 6.5 is obtained. A preferred pH adjusting agent is citric acid.

Additional features may be understood by referring to the following detailed description and examples.

DETAILED DESCRIPTION OF THE INVENTION

The present invention is a locking composition for vascular access device or intravascular delivery device comprising:
i) a carrier, such as water;
ii) about 35% to about 70%, preferably about 40% to about 60% and most preferably about 45% to about 55%, of a viscosity increasing agent; and
iii) about 1% to about 10%, preferably about 2% to about 8% and most preferably about 3% to about 6%, of an anticoagulant.

The composition should be free of heparin and alcohols, especially $C_1$ to $C_{12}$ alcohols.

The water that may be used for preparing the present invention can be any type of water, such as distilled water commonly used to prepare pharmaceutical preparations (some of which are described in the United States Pharmacopeia) and include, but are not limited to, water for injection, sterile water for inhalation, sterile water for injection, sterile water for irrigation, purified water and sterile purified water.

The viscosity-increasing agents useful in the present invention include, but are not limited to, glycerol, protein-based colloidal substances, dextrose, dextran and combinations of the forgoing. The preferred viscosity-increasing agent is glycerol. If glycerol is employed as the viscosity-increasing agent, it is believed the glycerol will impart antibacterial properties to the locking composition and thereby avoid the need for the addition of separate antibacterial and antimicrobial agents. The viscosity-increasing agent should be present in the locking composition in an amount about 35% to about 70%, preferably about 40% to about 60% and most preferably about 45% to about 55%, weight to volume of carrier.

The anticoagulant useful in the present invention is any anticoagulant commonly known in the pharmaceutical arts such as riboflavin, citrates, ethylene diamine tetracetic acid, warfarin or combinations of the foregoing. It is preferred that the anticoagulant not be heparin or any animal derivative or byproduct. In a preferred embodiment of the present invention, the anticoagulant is a citrate such as an ester of citric acid, i.e triethyl citrate or a citrate salt such as sodium citrate or other pharmaceutically acceptable salt. The anticoagulant should be present in the locking composition in an amount of about 1% to about 10%, preferably about 2% to about 8% and most preferably about 3% to about 6%, weight of anticoagulant to volume of carrier.

In one embodiment the amount of the viscosity of the locking composition should be about 20 mPa·s to about 50 mPa·s, preferably about 25 mPa·s to about 45 mPa·s and most preferably about 30 mPa·s to about 40 mPa·s. The viscosity can be measured by any means commonly known in the pharmaceutical arts including but not limited to the use of commercially available equipment such as an Ostwald Viscometer, an Hoeppler Viscometer, or a Brookfield Viscometer. A more detailed discussion of methods and apparatus for determining the locking composition's viscosity can be found in Chapter 17 of Physical Pharmacy, $4^{th}$ ed., by Alfred Martin.

The density of the locking composition should be greater than the density of a subject's blood. For example, human blood is known to range (depending upon the temperature and age of the patient) from about 1.02 g/ml to about 1.1 g/ml. Therefore, the present invention for use in humans should exhibit a density greater than 1.1 g/ml, preferably greater than about 1.12 gm/ml and most preferably greater than 1.13 gm/ml. The density can be measured by any means commonly known in the pharmaceutical arts. Some acceptable methods for measuring density of the locking composition are described in U.S. Pat. No. 4,929,242 and on pages 443-446 of Physical Pharmacy, 4$^{th}$ ed., by Alfred Martin.

The pH of the locking composition should be in the range of about 5.5 to about 8, preferably about 5.8 to about 7.5 and most preferably about 6.0 to about 7.0. The pH of the locking composition may be adjusted to the desired level once the appropriate density and viscosity are obtained. The pH may be adjusted by any means commonly known in the pharmaceutical arts such as the addition of a pharmaceutically acceptable acid or base to the locking composition. In a preferred embodiment, citric acid is added to the locking composition to adjust the pH to an appropriate level. The locking composition may also optionally employ a buffering agent to assist in controlling and maintaining the desired pH of the locking composition. The selection of an appropriate buffering agent is within the skill or the ordinary artisan.

The locking composition should be an isotonic composition or a hypertonic composition with respect to the subject's blood. The tonicity may also be referred to as a measurement of the osmolality of the locking composition. Tonicity or osmolality describes the concentration of solutes in a given solution. An isotonic composition exhibits a tonicity essentially equal to the tonicity of a subject's plasma. When employed in a normally hydrated subject, an isotonic composition does not cause a significant shift of water between the subject's blood vessels and cells. A hypertonic composition exhibits a tonicity higher than the tonicity of a subject's plasma. When employed in a normally hydrated subject, a hypertonic composition causes a shift of water toward the hypertonic composition in an effort to equilibrate the solute concentration. Methods for determining the tonicity or osmolality of the locking composition are described in U.S. Pat. No. 4,929,242 and on pages 137-140 of Physical Pharmacy, 4th ed., by Alfred Martin. An additional discussion can be found in the paper presented by Marc Stranz at the May 2005 INS Annual Conference entitled "The Implications of Osmolality, Osmolarity and pH in Infusion Therapy.

In one embodiment of the present invention, the osmolality of the locking composition should be greater than the osmolality of human blood. In this embodiment, the osmolality of the locking composition should be greater than 300 mOsm/L, preferably greater than 320 mOsm/L, and more preferably greater than about 350 mOsm/L.

The locking composition in accordance with the present invention should prevent fouling and/or plugging of a subject's vascular access device or intravascular delivery device for at least about eight (8) hours, preferably about 8 to about 24 hours.

The locking composition in accordance with the present invention should be stable to changes in pH and osmolality, during long term storage. The locking composition should also be resistant to bacterial and microbial growth during long term storage. For example, the locking composition in accordance with the present invention should exhibit less than a 1.0 unit change of pH, preferably less than a 0.5 unit change, in the pH after storage at 25° C. and 60% relative humidity for at least six (6) months, preferably one (1) year, when the locking composition is stored in an appropriate container such as a sterile and sealed syringe or a glass vial. Alternatively, the locking composition in accordance with the present invention should exhibit less than a 1.0 unit change of pH, preferably less than a 0.5 unit change, in the pH after storage at 40° C. and 75% relative humidity for at least one (1) month, preferably three (3) months, when the locking composition is stored in an appropriate container such as a sterile and sealed syringe or a glass vial.

The locking composition in accordance with the present invention should also be sterile and thereby prevent the growth of bacteria and microbes upon storage and, more importantly, during use. An appropriate test for determining if the locking composition is sterile is described in test <71> of the USP 25.

One embodiment of the present invention incorporates high amounts of glycerol which impart antimicrobial and antibacterial properties to the composition and thereby avoids the need for the use of additional or separate antimicrobial agents such as alcohols. Another embodiment of the present invention allows the locking composition to undergo a sterilization step after it is prepared and, more preferably, after it is packaged for use.

The locking composition in accordance with the present invention should prevent fouling and/or plugging of a subject's vascular access device or intravascular delivery device for at least about eight (8) hours, preferably about 8 to about 16 hours and more preferably about 8 to about 24 hours.

Another aspect of the present invention also includes a method of using the described locking compositions to maintain the patency of a vascular access device or intravascular delivery device. The method comprises the steps of:
  i) inserting a vascular access device or intravascular delivery device such as a catheter, cannulae, tube, injection ports, hollow needles, and the like into a subject, preferably a mammal such as a dog, cat, horse, pig or cow and most preferably a human; and
  ii) inserting the locking composition of the present invention into the lumen of the vascular access device or intravascular delivery device.

The locking composition can be inserted into the lumen of the vascular access device or intravascular delivery device by a syringe. One embodiment of this aspect of the invention employs a syringe that is prefilled with an appropriate amount of the locking composition which corresponds to the volume of the vascular access device or intravascular delivery device lumen. The prefilled syringe thereby allows the health care provider to quickly insert the vascular access device or intravascular delivery device into the subject and fill the vascular access device or intravascular delivery device lumen with the required amount of the locking composition. For example, if the lumen of a catheter has a volume of 5 ml, the prefilled syringe accompanying the catheter will contain 6 ml of the locking composition.

Alternatively, the locking composition may be provided in a standard glass or plastic container such as a bottle, vial or bag. The container may contain one or more treatment amounts of the locking composition. Appropriately measured amounts of the composition may be removed from the container and inserted into the lumen of the vascular access device or intravascular delivery device.

Another embodiment of the present invention is a kit comprising:
  i) a container comprising the locking composition for maintaining the patency of a vascular access device or intravascular delivery device; and
  ii) an instruction set describing the use of the locking composition. The container may comprise about 1 ml to about 500 ml of the locking composition or other appropriate amounts of the locking composition such as 10, 20, 25, 50 or 100 ml. The kit may further comprise a vascular access device or intravascular delivery device such as a catheter and a syringe for filling the vascular access device or intravascular delivery device with the locking composition once the vascular access device or intravascular delivery device has been inserted into a subject.

A preferred embodiment of the present invention comprises a kit comprising:
i) a vascular access device or intravascular delivery device for inserting into a subject, preferably a human subject;
ii) at least one prefilled syringe containing a premeasured amount of the locking composition that corresponds to the volume of the lumen of the vascular access device or intravascular delivery device from step i; and
iii) optionally an instruction set for providing a health care provider with instructions for inserting the vascular access device or intravascular delivery device into the subject and inserting the locking composition from the prefilled syringe into the lumen of the inserted vascular access device or intravascular delivery device.

As indicated previously, the preferred embodiment of the present invention consists essentially of water, glycerol and a citrate, preferably sodium citrate. The viscosity of a glycerol base in this embodiment is believed to reduce the translocation of blood into the vascular access device or intravascular delivery device, and thus minimizes the frequency of administration required to maintain a subject's vascular access device or intravascular delivery device. The presence of the citrate, acts as an anticoagulant in blood and is known to be more compatible in vitro with red blood cells than heparin.

The present invention, including the proposed citrate-glycerol embodiments, solves longstanding art-recognized problems associated with clotting in vascular access devices or intravascular delivery devices. For example, glycerol (being a highly viscous product) reduces the frequency of flushing because of its tendency to stay within the lumen of the vascular access device or intravascular delivery device and not mix easily with the blood. Furthermore, the presence of the citrate prevents coagulation, such as by chelating calcium ions that are cofactors for several enzymes in the clotting cascade. Accordingly, the combination of ingredients in solution will require that indwelling catheters would need to be flushed no more than once about every 12 hours; this represents a significant improvement and advantage over the current standard of care involving heparin-based anticoagulants.

It is believed that the sodium citrate-glycerol solutions may also present additional advantages. First, sodium citrate is a well-studied anticoagulant for blood transfusion collection bags and is known to have good compatibility with red blood cells. It is also well known that heparinized blood collection tubes are not acceptable for performing complete blood counts in clinical laboratories due to the crenation of the red blood cells. Also, whereas heparin is widely used for systemic anticoagulation in patients with hypercoagulable tendencies, sodium citrate is metabolized too quickly to be useful in this regard. The inventors believe that the occasional patient that becomes systemically affected by the prolonged use of heparin flush in long term indwelling catheters would be prevented from developing bleeding tendencies by the use of a citrate based anticoagulant instead. Also, citric acid and glycerol are known to have antimicrobial properties and thus might provide a synergistic and/or improved benefit for infection prevention, thus solving another significant problem for long-term indwelling vascular access devices or intravascular delivery devices.

EXAMPLES

Example 1

Materials and Methods

In the this example, the following commercially available materials were used: Glycerol 99.7% (KIC Chemicals); Anhydrous sodium citrate and citric acid (Sigma); Sterile water for injection (Hospira); Xylene (Fisher Scientific); pH meter (Accumet®, Fisher Scientic); Analytical balance (Adventurer®, OHAUS); Winged infusion/collection sets with 21 g needles (Vacuette®, Greiner Bio-One); Vacutainer® holder (Becton Dickinson); 3 cc vacutainers (Monoject® blood collection tubes, Sherwood Medical); Heparin/saline solution, 100 IU/mL (Hep-lock®, Elkins-Sinn, Inc.); and NZW rabbits (Covance) as a source of fresh blood.

Preparation of Glycerol-Citrate and Heparin Solutions

First, different concentrations (25%, 20%, 15%, 10%, and 5%) of citrate stock solutions were prepared with sodium citrate and citric acid at a ratio of 10:1 to achieve a pH range between 6.0 and 7.0. In order to make 25% stock solution, 2.25 g of sodium citrate and 0.25 g of citric acid were measured and dissolved in 10 mL of sterile water. For 20% solution, 1.82 g of sodium citrate and 0.18 g of citric acid were dissolved in 10 mL of sterile water. For the 15% solution, 1.36 g of sodium citrate and 0.136 g of citric acid were dissolved in 10 mL of sterile water. For a 10% stock solution, 0.91 g of sodium citrate and 0.09 g of citric acid were measured and dissolved in 10 mL of sterile water, and, finally, for a 5% stock solution, 0.455 g of sodium citrate and 0.045 mg of citric acid were dissolved in 10 mL of sterile water to form an aqueous stock solution. The final pH for all of the above concentrations of aqueous stock solutions was measured using a pH meter.

Once the different concentrations of aqueous stock solutions were prepared, then each stock solution was diluted 5-fold with glycerol to generate the final glycerol-citrate solutions that thus contained 80% glycerol/20% aqueous with final citrate concentration of 5%, 4%, 3%, 2%, and 1%. The final pH for each of the solutions was read using a pH meter.

Using a syringe with a 23 gauge needle, triplicate 0.5 mL aliquots of each solution were transferred into 3 cc "red-top" blood collection tubes (Vacutainer®), taking care to maintain the vacuum in the tube. Commercially prepared heparin-saline solution (Heplock® 100 IU/mL, 0.5 cc) was also added to 3 other tubes to serve as the comparator group.

Collection and Evaluation of Blood

Three rabbits were randomly selected, and the ear in which the artery is more conspicuous was chosen for blood collection. The fur covering the aural artery on the medial aspect of the ear was gently removed and the site cleaned with isopropyl alcohol. Xylene was applied topically over the artery to facilitate vasodilation. Using winged blood collection sets, 2.0-2.5 mL of fresh blood was collected directly into each sample tube, and the tubes were turned several time to mix the components. One rabbit was used for each replication of the experimental groups. The samples were stored at room temperature and checked 24 and 48 hours later for the presence of blood clots in the tubes. A drop of any non-clotted samples was placed on a glass microscope slide, and a blood smear was made to evaluate RBC morphology microscopically. The tubes were placed in a refrigerator and checked again for clotting at 10 days.

Results

The pH for stock solutions ranging from concentration 25% to 5% were as follows: 25% aqueous stock solution=6.17; 20%=6.18; 15%=6.21; 10%=6.23; and 5%=6.21. The pH values for the final glycerol-citrate solutions read as follows: 5%=6.34; 4%=6.40; 3%=6.46; 2%=6.52; and 1%=6.62. It was notable during the blood collection procedure that the arterial blood spurting into the collection tube did not readily mix with the glycerol-nitrate solutions; the blood sat on top of the glycerol layer until several turns of the test tube facilitated their mixing. At 24 and 48 hours, the only clotted samples were the three 1% citrate-glycerol tubes (the blood was a solid clot in these tubes). All other samples remained fluid with no grossly visible evidence of blood clotting.

Review of the blood smears at 400× magnification at 24 and 48 hours revealed that the morphology of the RBCs was observed to be normal in the glycerol-citrate groups (2%-5%), whereas all RBCs in the heparin-saline tubes were substantially crenated and spiculated. After the blood was stored for 10 days, it was noted that 1 of the 3 tubes in the 2% citrate group was clotted; the other two remained fluid. In summary, the results on the above experiments showed that the blood in the tubes with 2-5% glycerol-citrate solution did not clot, along with the heparin-saline comparator group.

Example 2

A locking composition in accordance with the present invention was prepared as follows: 30 g of sodium citrate was added to 400 ml of water for injection and mixed thoroughly until dissolved. 1 g of citric acid was then added to the sodium citrate mixture and mixed thoroughly until the citric acid was dissolved. The pH of the sodium citrate/citric acid mixture was measured. The target pH was 6.3 with an acceptable range of 6.0 to 6.5. If the pH was above 6.5, additional quantities of citric acid were added in 100 mg increments until the pH was within the acceptable range. 500 g of glycerol USP was added to the sodium citrate/citric acid mixture and mixed thoroughly. Additional water for injection was added to obtain a final volume of 1000 ml. The pH of the final volume composition was checked to insure the range of 6.0 to 6.5 was maintained. If the pH was outside this target range, it was adjusted to the target range. The resulting composition was filtered through a 0.22 micron filter and filled into 1 ml syringes. Each syringe contained 1 ml of locking composition with the following composition:

| INGREDIENT | CONCENTRATION |
| --- | --- |
| Sodium Citrate USP Anhydrous | 3.0% wt/v |
| Citric Acid USP Anhydrous | 0.1% wt/v |
| Glycerol USP | 50% wt/v |
| Water for Injection | 100% wt/v |

Example 3

A locking composition in accordance with the present invention was prepared according to the procedure outlined in Example 2 except the locking composition had the following final composition:

| INGREDIENT | CONCENTRATION |
| --- | --- |
| Sodium Citrate USP Anhydrous | 4.0% wt/v |
| Citric Acid USP Anhydrous | 0.1% wt/v |
| Glycerol USP | 50% wt/v |
| Water for Injection | 100% wt/v |

The locking composition of Example 3 and reference compositions A (comprising water and 4% sodium citrate) and B (comprising water and 50% glycerol) were tested and found to have the following properties:

| | Test Item | | |
| --- | --- | --- | --- |
| Test | 4% sodium citrate | 4% sodium citrate in 50% glycerol | 50% glycerol |
| pH | 6.00 | 6.10 | 2.8 |
| Specific gravity | 1.026 | 1.141 | 1.116 |
| Total sodium | 1.24% | 1.13% | 15 PPM |
| Viscosity (Spindle No.: 1, RPM: 200 & Temperature: 24.8° C.) | Result: 15.9 mPa·s Torque: 31.1% | Result: 36.2 mPa·s Torque: 71.7% | Result: 34.7 mPa·s Torque: 69.5% |

The viscosity is measure using Brookfield DV-II+ having capacity to measure viscosity between 50-100000 mPa·s.

The pH was measured using a THERMO brand pH meter, Model: Orion 3-star.

The specific gravity using a Pycnometer.

The composition of Example 3 was tested in New Zealand White Rabbits to evaluate its effects in controlling/delaying clot formation. The control in the experiment was the commercially available HEPARIN LOCK FLUSH® a 100 IU/ml heparinized saline solution obtained from Abraxis Pharmaceuticals.

In Test 1, six adult rabbits were randomly grouped into 3 groups containing 2 animals each. All 3 groups were kept in animal restrainers, and 22 G 0/98 IN (0.8×25 mm) BD VEnflon™ cannula were inserted in marginal ear vein of left and right ears. Heparinized saline of 100 IU/ml concentration was injected 0.5 ml/marginal vein as IV injection and the amount to be filled in the cannula. The cannula was allowed to be at the site until the time of observations. The observations were as follows:

TEST 1

| | Test Item: Heparinized saline | | | | | |
| --- | --- | --- | --- | --- | --- | --- |
| Time point | Animal No. 1 | Animal No. 2 | Animal No. 3 | Animal No. 4 | Animal No. 5 | Animal No. 6 |
| 4 hrs after injection | NCD* | NCD* | — | — | — | — |
| 8 hrs after injection | — | — | NCD* | NCD* | — | — |
| 12 hrs after injection | — | — | — | — | CD** | NCD* |
| 24 hrs after injection | CD** | CD** | — | — | — | — |

NCD*—No clot detected: Withdrawal of blood was possible after application of IPA for dilatation of vein
CD**—Clot detected: NOT ABLE to withdraw the blood after application of IPA for dilatation of vein In Test 2, six adult rabbits were randomly grouped into 3 groups containing 2 animals each. All 3 groups were kept in animal restrainers, and 22 G 0/98 IN (0.8×25 mm) BD VEnflon™ cannula were inserted in marginal ear vein of left and right ears. Group I rabbits were injected with a sodium citrate 4% solution prepared according to the procedure of Example 3 except the glycerol was not added. Group II rabbits were injected with the locking composition of Example 3. Group III rabbits were injected with a 50% glycerol composition prepared according to the procedure outlined in Example 3 except no sodium citrate or citric acid was added. All rabbits were injected 0.5 ml/marginal vein as IV injection and the amount to be filled in the cannula. The cannula was allowed to be at the site until the time of observations. The observations were as follows:

TEST 2

| | Test Item:<br>4% Sodium Citrate | | | Test Item:<br>4% Sodium Citrate<br>in 50% Glycerol | | | Test Item:<br>50% Glycerol | | | | |
|---|---|---|---|---|---|---|---|---|---|---|---|
| | Animal No. 1 | | Animal No. 2 | | Animal No. 3 | | Animal No. 4 | | Animal No. 5 | | Animal No. 6 | |
| Time point | LE | RE | LE | RE | LE | RE | LE | RE | LE | RE | LE | RE |
| 24 hrs after injection | CD** | CD** | CD** | CD** | NCD* | CD** | CD** | CD** | CD** | CD** | CD** | CD** |

NCD*—No clot detected: Withdrawal of blood was possible after application of IPA for dilatation of vein
CD**—Clot detected: NOT ABLE to withdraw the blood after application of IPA for dilatation of vein The results of Tests 1 and 2 suggest the locking composition of Example 3 can delay fouling and clogging of vascular access devices or intravascular delivery devices.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

I claim:

1. A locking composition comprising:
   i) water;
   ii) an antibacterial or antimicrobial agent comprising:
      (a) about 35% to about 70% by weight of the composition of glycerol; and
      (b) about 3% to about 6% by weight of the composition of a sodium citrate; and
   iii) optionally a pharmaceutically acceptable acid or base;
   wherein the composition does not contain an additional antibacterial or antimicrobial agent.

2. The locking composition of claim 1 wherein the composition comprises about 40% to about 60% of glycerol.

3. The locking composition of claim 2 wherein the composition comprises about 45% to about 55% of glycerol.

4. The locking composition of claim 1, wherein the composition comprises a pharmaceutically acceptable acid or base.

5. The locking composition of claim 4, wherein the pharmaceutically acceptable acid or base is present in an amount sufficient to adjust the pH of the composition from about 5.8 to about 7.5.

6. The locking composition of claim 2, wherein the composition comprises about 60% glycerol.

7. A locking composition consisting of:
   i) water;
   ii) an antibacterial or antimicrobial agent consisting of:
      (a) 40-60% by weight of the composition of glycerol;
      (b) 3-6% by weight of the composition of sodium citrate; and
   iii) optionally an organic acid to adjust the pH of the composition from about 6.0 to about 7.0.

8. A method for maintaining the patency of a vascular access device or intravascular delivery device comprising the steps of:
   i) inserting a vascular access device or intravascular delivery device into a subject; and
   ii) inserting the locking composition of claim 1 into the lumen of the vascular access device or intravascular delivery device.

9. The method of claim 8 further comprising the step of filing a syringe with the locking composition of claim 1 in an amount equal in volume to the volume of the lumen of the vascular access device or intravascular delivery device and inserting the contents of the filled syringe into the lumen of the vascular access device or intravascular delivery device inserted into the subject.

10. A kit comprising a container comprising the locking composition of claim 1 and an instruction set describing the use of the locking composition.

11. The kit of claim 10 further comprising a vascular access device or intravascular delivery device.

12. The kit of claim 11 wherein the container is a syringe.

* * * * *